United States Patent [19]
De Goicoechea et al.

[11] Patent Number: 5,383,927
[45] Date of Patent: Jan. 24, 1995

[54] NON-THROMOGENIC VASCULAR PROSTHESIS

[75] Inventors: George L. De Goicoechea, Cassis, France; John O. Hudson, Clearwater, Fla.

[73] Assignee: Intervascular Inc., Clearwater, Fla.

[21] Appl. No.: 47,799

[22] Filed: Apr. 15, 1993

Related U.S. Application Data

[63] Continuation of Ser. No. 879,345, May 7, 1992, abandoned.

[51] Int. Cl.⁶ .................. A61F 2/06; A61F 2/04
[52] U.S. Cl. .......................... 623/1; 623/12; 600/36
[58] Field of Search ............... 623/1, 11, 12; 128/DIG. 8; 600/36

[56] References Cited

U.S. PATENT DOCUMENTS

| | | | |
|---|---|---|---|
| 4,441,215 | 4/1984 | Kaster | 623/1 |
| 4,806,595 | 2/1989 | Noishiki et al. | 623/12 |
| 4,822,361 | 4/1989 | Okita et al. | 623/12 |
| 4,833,200 | 5/1989 | Noishiki et al. | 525/54.2 |
| 5,108,424 | 4/1992 | Hoffman, Jr. et al. | 623/1 |

FOREIGN PATENT DOCUMENTS

| | | | |
|---|---|---|---|
| 0092414 | 10/1983 | European Pat. Off. | 600/36 |
| 8800813 | 2/1988 | WIPO | 623/1 |

*Primary Examiner*—David Isabella
*Assistant Examiner*—Debra S. Brittingham
*Attorney, Agent, or Firm*—Lerner, David, Littenberg, Krumholz & Mentlik

[57] ABSTRACT

The present invention provides vascular prostheses free of any substance that counteracts an anticoagulant comprising a base material, the base material having inner and outer surfaces, wherein the outer surface has a layer of a material capable of reducing the porosity of said prosthesis to blood or body fluid and a coating of compounded heparin bound thereon, and the inner surface has a coating of compounded heparin bound thereon, the compounded heparin comprising heparin and a cationic surfactant. The present invention also provides a method for forming a vascular prosthesis. The vascular prostheses of the present invention exhibit low porosity at the time of implantation of the prosthesis thereby obviating the need for pre-clotting the prosthesis to avoid leakage or hemorrhaging of blood through the prosthesis. The compounded heparin coating of the vascular prostheses of the invention prevents or slows down blood clotting which leads to the build up of natural tissue within the interstitial spaces of the prosthesis and the build-up of a thin, even, well-defined and well-adhered pseudo-intima on the inner surface of the prosthesis.

20 Claims, 1 Drawing Sheet

NON-THROMOGENIC VASCULAR PROSTHESIS

This is a continuation of application Ser. No. 07/879,345 filed May 7, 1992 now abandoned.

FIELD OF THE INVENTION

This invention relates to vascular prostheses and more particularly to a vascular prosthesis having a coating of ionically bonded heparin to act as an anticoagulant.

BACKGROUND OF THE INVENTION

The replacement of segments of human blood vessels with vascular grafts is well known in the art. Among the accepted and successful vascular graft implants are those which are formed from a biologically compatible material which retains an open lumen to permit the flow of blood through the graft after implantation.

Vascular prosthesis made of knitted or woven Dacron ® polyester have been used for many years in a variety of constructions. Common textile prostheses, made from Dacron ® polyester, are very porous and require preclotting with the patient's blood prior to surgery in order to prevent hemorrhaging after implantation. Recent developments have employed coating the prosthesis, which enables the prosthesis to be implanted without preclotting. Coatings of different materials have been used, including biodegradable materials such as albumin, collagen and gelatin, as well as non-biodegradable materials such as elastomeric polymers.

Greco et al., U.S. Pat. No. 4,879,135 issued Nov. 7, 1989 discloses vascular grafts with a coating, respectively, of an anionic or cationic surfactant and an oppositely charged drug bound to the surfactant. The surfactant and oppositely charged drug are ionically bound.

Greco et al, U.S. Pat. No. 4,444,133 and Greco et al, U.S. Pat. No. 4,740,382 disclose vascular grafts coated with a cationic surfactant (TDMAC) and a negatively charged antibiotic.

Hu et al, U.S. Pat. No. 5,032,666 issued Jul. 16, 1991 discloses vascular grafts having a coating of thermoplastic fluorinated polyurethane urea (FPUU) having free amino groups which are then reacted with heparin or other antithrombogenic agent to covalently bond the compound to the FPUU coating.

Mano et al., U.S. Pat. No. 4,229,838 issued Oct. 28, 1980 discloses vascular grafts having a coating of polyethyleneimine that has been water-insolubilized by cross-linking with heparin ionically bound to the polyethylemeimine.

Mano et al., U.S. Pat. No. 4,321,711 issued Mar. 30, 1982 discloses a vascular graft having an anticoagulant substance such as heparin bound to the inner surface and a porous elastomer coating on the outside of the graft which contains a substance which counteracts the anti-coagulant substance.

However, these various coating approaches do not solve the problem of reducing the porosity of the prosthesis at the time of implantation so as to obviate the need for pre-clotting procedures, while at the same time reducing the thrombogenicity of the prosthesis to prevent clotting after implantation and promote the build up of a thin, even, well-defined and well-adhered pseudo-intima in the prosthesis. Therefore, there is a need for a vascular prosthesis which exhibits low porosity at the time of implantation of the prosthesis in order to obviate the need for pre-clotting which does not require a substance that counteracts an anti-coagulant, but which also allows for rapid build up of natural tissue within the interstices of the fabric of the prosthesis to promote good healing and prevent clotting.

SUMMARY OF THE INVENTION

The present invention provides a vascular prosthesis free of any substance that counteracts an anti-coagulant comprising a base material, the base material having inner and outer surfaces, wherein the outer surface has a layer of a material capable of reducing the porosity of the prosthesis to blood or body fluid and a layer of compounded heparin bound thereon, and the inner surface has a layer of compounded heparin bound thereon. The compounded heparin employed in the grafts of the present invention preferably comprises heparin ionically bonded with the cationic surfactant.

The coating of compounded heparin reduces thrombogenicity of the prosthesis by preventing or slowing down clotting, and promotes the build up of a thin, even, well-defined and well-adhered pseudo-intima on the inner surface of the vascular prosthesis. The material capable of reducing the porosity of the prosthesis obviates the need for pre-clotting procedures prior to implantation of the prosthesis.

The present invention also provides a method of forming a vascular prosthesis comprising a base material having inner and outer surfaces, comprising the steps of applying a material capable of reducing porosity of the vascular prosthesis to the outer surface of the base material to form a layer of the material capable of reducing the porosity of the vascular prosthesis on the outer surface; and applying compounded heparin to the layer of material from step (a) and to the inner surface of said vascular prosthesis, the compounded heparin comprising heparin and a cationic surfactant, to form a layer of the compounded heparin on the layer of the material capable of reducing porosity of the vascular prosthesis and a layer of compounded heparin on the inner surface of the vascular prosthesis. The vascular grafts of the invention may also be formed by applying the compounded heparin prior to applying the material capable of reducing porosity of the vascular graft such that the layer of compounded heparin is formed on the inner and outer surfaces of the base material and the lawyer of material capable of reducing porosity of the vascular prosthesis is formed on the layer of compounded heparin on the outer surface of the prosthesis.

This invention is more particularly pointed out in the appended claims and is described in its preferred embodiments in the following description.

DETAILED DESCRIPTION OF THE INVENTION

Figure 1B:
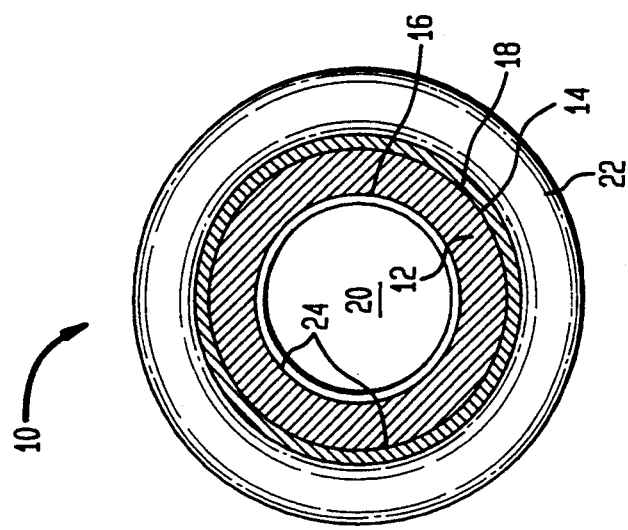
FIG. 1b is a schematic of a cross-sectional view of the same vascular prosthesis of the invention having a collagen layer bound on the outer surface and a coating of heparin on the inner surface and on the collagen layer.

The vascular prostheses of the present invention are free of any substance that counteracts an anti-coagulant and exhibit low porosity at the time of implantation of the prosthesis thereby obviating the need for pre-clotting the prosthesis to avoid leakage or hemorrhaging of blood through the prosthesis. The compounded heparin coating of the vascular prostheses of the invention prevents or slows down blood clotting which leads to the build up of natural tissue within the interstitial spaces of the prosthesis and the build-up of a thin, even, well-defined and well-adhered pseudo-intima on the inner surface of the prosthesis. Thus, the vascular prostheses of the invention are convenient to use and provide a good substrate for regrowth of blood vessel tissue.

The base material of the prosthesis is preferably a bio-compatible polymeric material that can be fabricated into a porous structure which will permit tissue ingrowth and maintain an open lumen for blood flow. Preferred base materials include polyethylene terephthalate (Dacron ® polyester). The base material may be woven, knitted, or cast into the desired shape for the prosthesis, depending on the type of material selected for use. Knitted prostheses are used mainly to replace diseased sections of arteries in the abdominal and peripheral areas of the body, while woven prosthesis are used mainly in the higher pressure thoracic areas. The vascular grafts of the invention can have any shape suitable for implantation into an animal such as a tubular shape, a bifurcated tubular shape, or be in the form of a sheet of material. Such flat sheets of material are known in the art as "patch grafts". Such patch grafts may have any size and configuration. Patch grafts are generally employed for repairing large blood vessels which do not require complete removal of tubular sections. A specialist form of patch graft is a thin strip of material having selvedged edges. The selvedged edge allows sutures to be placed at the very edge of the patch in order to make a very small neat suture line without risk of the sutures pulling out of the fabric. This specialist patch is generally used to close the carotid artery following a carotid endorectomy. Such carotid patches are typically about 75 mm long and from about 4 mm to 16 mm in width. As used herein, the term biocompatible refers to material that is suitable for implantation into the body of an animal, particularly the human body. Materials may be formed into vascular grafts according to the methods known in the art, or suitable grafts may be obtained from commercial suppliers such as InterVascular, Clearwater, Fla. (InterVascular Knitted Micron and InverVascular Woven LP).

The vascular prostheses of the invention may optionally be radially supported by a synthetic polymeric material. Preferably the synthetic polymer is formed around the outer surface along the length of the graft to form a spiral or sleeve of material to support the prosthesis. The radial supporting material may also be formed integrally into the wall of the prosthesis itself. A preferred synthetic polymer for support of the vascular prosthesis is a polypropylene monofilament.

As used herein, the inner surface of the graft is the surface that is in contact with the flow of blood, whereas the outer surface of the graft is the surface not in contact with the flow of blood and is in contact with other body tissues. In the case of a tubular shaped graft the inner surface is the surface in the lumen of the graft that will be in contact with the flow of blood, and the outer surface is the opposite surface on the outside of the graft that will be in contact with other body tissues when implanted into an animal. In the case of a patch graft, the inner surface is the surface in contact with the flew of blood and the outer surface is the surface in contact with other body tissues.

The prostheses are coated with a layer or coating of a material capable of reducing the porosity of the prosthesis to blood or other body fluids. Vascular prostheses are typically permeable to blood and other body fluids, especially in applications where the pressure of the blood within the prosthesis is high, and blood or other fluid leaks through the prosthesis into surrounding tissues. Thus the material capable of reducing porosity of the vascular prosthesis acts as a barrier to the seeping of blood or other fluid through the walls of the prosthesis into surrounding tissue and renders them impermeable or substantially impermeable to the blood or other body tissue. The material capable of reducing the porosity of the prosthesis may be selected from biodegradable and non-biodegradable materials. A preferred biodegradable material is collagen. Suitable non-biodegradable materials include silicon based elastomeric polymers such as Silastic ® materials, and polyurethane. The material capable of reducing the porosity is applied to the inner or outer surface or both of the prosthesis such that a layer of material is formed that is effective to obviate the need for pre-clotting the prosthesis before it is inserted into an animal, i.e. the thickness of the layer formed renders the prosthesis impermeable or substantially impermeable to blood or other body fluid. The thickness of the layer of material capable of reducing porosity of the vascular prosthesis is preferably from about 0.05 mm to about 0.1 mm in thickness; more preferably from about 0.06 to about 0.09 mm in thickness; most preferably from about 0.06 to about 0.08 mm in thickness.

When collagen is employed as the material capable of reducing porosity of the vascular prosthesis, the collagen may be applied such that it impregnates intimately into the interstitial spaces of the fabric of the base material. Alternatively, the collagen may be formed into a thin membrane or film adhered to the surface of the base material and not extending into the interstitial spaces of the base material. The porosity reducing coating comprising a biodegradable material may be adhered to the outer surface of the base material, the inner surface of the base material, or both the inner and outer surfaces. The biodegradable material may also be applied to the inner surface of the base material, or on top of an underlayer of compounded heparin. In embodiments of the invention having the biodegradable material on both the inner and outer surfaces of the base material, the layer of biodegradable material on the interior of the prosthesis is preferably thinner than the layer on the outer surface. The layer on the inner surface of the base material can be thinner than the layer on the outer surface since the blood pressure forces the inner layer against the base material of the prosthesis. The layer on the outer surface is prevented from separating from the base material only due to adhesive bonds. For embodiments of the invention where the porosity reducing coating is a non-biodegradable material, the porosity reducing coating is applied only to the outer surface of the base material and is preferably applied to the base material before the heparin coating is applied.

In preferred embodiments of the invention, collagen is employed as the biodegradable material capable of reducing porosity of the vascular graft. The collagen is selected to be compatible with the species of animal into which the prosthesis will be inserted. For use in humans, bovine collagen is preferred since it is widely available and causes few adverse reactions. A preferred type of bovine collagen is derived from the achilles tendon. Collagen is preferably obtained in the form of compressed collagen fiber sheets made from highly purified, insoluble, type 1, bovine achilles tendon collagen fiber, which may be obtained commercially from suppliers such as Bioplex, Vaals, Holland. The collagen in the sheet form is not cross-linked and is similar to that used as a hemostat sponge. The sheets of collagen are chopped into small pieces and made into an aqueous fine dispersion or slurry containing from about 5 grams per liter to about 12 grams of collagen per liter of dispersion. More preferably, collagen is present in the aqueous dispersion in the amount of about 10 grams per liter $\pm$10%. A wetting agent is added to the dispersion in an amount effective to wet the collagen. A suitable wetting agent is polyoxyethylenesorbitan monolaurate (Tween 20 ® Fisher Scientific Corp, Springfield, N.H.) which is added in amounts of about twelve grams per liter of dispersion. A plasticizer is also added to the dispersion. A suitable plasticizer is glycerol (Fisher Scientific Corp., Springfield, N.H.) which is added in amounts of about ten grams per liter of dispersion. This process results in a gel like slurry.

The collagen may be applied to the base material such that it is intimately impregnated into the interstitial spaces of the base material by dipping the prosthesis into an aqueous dispersion of collagen and subsequently cross-linking the collagen with a cross-linking agent such as glutaraldehyde.

Alternatively, when the collagen is applied as a thin membrane or film adhered to the surface of the base material and not extending into the interstitial spaces of the base material, or when it is applied over a layer of compounded heparin as a thin membrane or film, an aqueous dispersion of collagen is cross-linked prior to application to the prosthesis. The collagen in the aqueous dispersion is cross-linked by adding a cross-linking agent such as glutaraldehyde and mixing for a length of time effective to cross-link the collagen but still provide a pliable aqueous dispersion that can be used for coating the vascular prosthesis. When glutaraldehyde is used as the cross-linking agent, the aqueous dispersion is stirred for about 20 hours with the glutaraldehyde (about 0.6 grams per liter of dispersion) and the cross-linking process can be terminated by the addition of glycine (about 1.0 grams per liter of dispersion).

When layers of collagen are applied to both the inner and outer surfaces or layers of compounded heparin, the inner layer of collagen is preferably substantially thinner than the outer layer. Differential thickness may be achieved by dipping the prosthesis one or more times in the aqueous dispersion of collagen to coat both the inner and outer surfaces or layers of compounded heparin and form a layer of collagen of a desired thickness, sewing shut the ends of the prosthesis, and redipping the closed-end prosthesis into collagen for further applications to form a thicker layer of collagen of desired thickness on the outer surface or layer of compounded heparin.

Compounded heparin is applied to the base material either over or under a layer of biodegradable material capable of reducing the porosity of the vascular graft. When a non-biodegradable material is used, the layer of compounded heparin is applied after or on top of the layer of non-biodegradable material. Compounded heparin as used in the present invention comprises heparin and a cationic surfactant. The heparin is preferably ionically bound to the cationic surfactant. Suitable cationic surfactants include tridodecylmethylammonium chloride (TDMAC) heparin and benzalkonium chloride. The coating of compounded heparin is ionically bound to either the base material or the layer of material capable of reducing the porosity of the prosthesis, depending on the embodiment of the invention. The compounded heparin penetrates into the interstices of the base material and coats the individual fibers of knitted or woven base materials and coats the pores of cast base materials. Thus, as referred to herein a coating of heparin on the inner or outer surface of the base material refers to compounded heparin deposited on the individual fibers of knitted or woven base materials or in the pores of cast base materials in amounts sufficient to coat the individual fibers or pores on the surface and in the interior of the base material, at least those fibers or pores adjacent to the surface, but not in amounts sufficient to form a film or layer on the surface of the base material. The compounded heparin is not soluble in either water or blood plasma, so that it stays bonded to the inner surface of the base material, also referred to as the luminal wall. Compounded heparin is applied to the prosthesis in amounts sufficient to serve as an anticoagulant, however, the amount preferably should not be sufficient to promote platelet clots and/or leukocyte reactions. Effective concentrations of compounded heparin range from about 2.5 to about 15 grams per square meter, which provides approximately 15 to 100 USP units of heparin per square centimeter of prosthesis surface. More preferably the compounded heparin is applied at a concentration of about 7 grams per square meter, providing 45 USP units per square centimeter. Compounded heparin can be prepared by ionically bonding heparin to a cationic surfactant using methods known in the art, or it can be obtained commercially through suppliers such as CIA Labs, St. Joseph, Mo.

Compounded heparin is applied to the vascular prosthesis by dipping the prosthesis into a solution containing compounded heparin for about 30 to about 60 seconds and then air drying the prosthesis. The solvent used for the solution will vary depending on the cationic surfactant used. For example, when the compounded heparin comprises TDMAC and heparin, the solvent is a mixture of 50% toluene and 50% petroleum ether. Where the compounded heparin comprises benzalkonium chloride and heparin, the solvent may be one of a number of different types known in the art, including methylene chloride or ethyl alcohol. The compounded heparin solution may be made in a variety of concentrations from about 0.5% to about 6% weight per volume. Since the amount of compounded heparin that will adhere to the base material or material capable of reducing porosity of the vascular prosthesis is proportional to the concentration of compounded heparin in the solution, the amount of compounded heparin may be controlled by solution strength, i.e. the greater the amount of compounded heparin in the solution, the greater the amount of compounded heparin applied to the surface of the base material or the material capable of reducing the porosity of the vascular prosthesis. The evaporation of the solvent leaves the solute (i.e. compounded heparin) adhered to the prosthesis.

Thus, the present invention provides vascular prostheses free of any substance that counteracts an anticoagulant and comprising a base material wherein the outer surface has a layer of a material capable of reducing the porosity of the prosthesis to blood or body fluid and a layer of compounded heparin bound thereon, and the inner surface has a layer of compounded heparin bound thereon. In one of the embodiments of the present invention, the layer of material capable of reducing the porosity of the prosthesis is bound to the outer surface of the vascular prosthesis and the layer of compounded heparin is bound to the layer of material capable of reducing the porosity of the vascular prosthesis. In another embodiment, the layer of compounded heparin is bound to the outer surface of the vascular graft and the layer of material capable of reducing the porosity of said vascular prosthesis is bound to the layer of compounded heparin. In a further embodiment of the invention, the inner surface of the prosthesis has a layer of compounded heparin and a layer of a biodegradable material capable of reducing porosity of the vascular prosthesis.

Figure 1A:
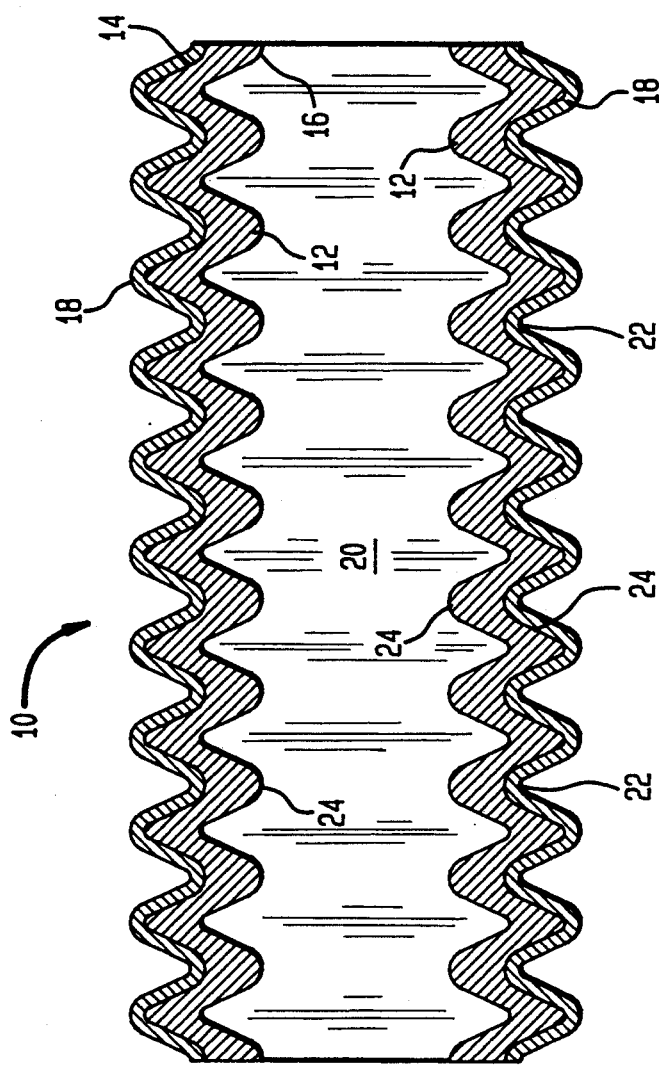
FIG. 1a is a schematic of a longitudinal cross-sectional view of a vascular prosthesis of the invention having a collagen layer bound on the outer surface and a coating of heparin on the inner surface and on the collagen layer.

A vascular prosthesis constructed and arranged in accordance with the present invention is shown in FIG. 1. FIG. 1a shows a schematic longitudinal cross-sectional view of a vascular prosthesis 10 of the invention. FIG. 1b shows a schematic cross-sectional view of the same prosthesis 10. The prosthesis in FIGS. 1a and 1b has a tubular shape and an inner lumen 20 extending through the length of the prosthesis. The inner surface 16 of the prosthesis 10 is in contact with the flow of blood when the prosthesis is implanted into an animal. The outer surface 14 of the prosthesis 10 has a collagen layer 18 bound thereon. The collagen layer is on the outer surface 14 and does not extend into the walls 12 of the prosthesis. In FIG. 1a the prosthesis 10 is shown with crimps 22 that strengthen the walls 12 of the prosthesis 10. A coating of compounded heparin 24 is bound to the inner surface 16 of the prosthesis 10 such that it coats the individual fibers of the prosthesis at the inner surface 16 and in the walls 12 of the prosthesis. A coating of compounded heparin 24 is also bound to the outer surface 14 of the prosthesis 10 such that it coats the individual fibers of the prosthesis at the outer surface of the prosthesis and in the walls 12 of the prosthesis.

In a preferred embodiment of the invention a Dacron® polyester fabric prosthesis is coated on its inner and outer surfaces with compounded heparin. Then a layer of cross-linked collagen is applied to the outer layer of compounded heparin, or both the inner and outer layers of compounded heparin so that the collagen forms a thin membrane or film. In the case of the prosthesis with inner and outer collagen layers, the inner layer is preferably substantially thinner than the outer layer. The collagen layer on the inner surface or inner compounded heparin layer is absorbed first, and the blood is allowed to permeate slowly into the interstices of the fabric of the base material. The outer layer of collagen prevents leakage of blood or other fluid from the prosthesis into surrounding tissue. The Dacron® fiber surface is mildly thrombogenic, which means that the blood would normally form a surface clot. The base material of the prosthesis of the present invention, however, has been coated with compounded heparin so that the clotting process is initially prevented and later controlled at a slow rate. This result is a slow tissue build up in the interstices of the fabric of the base material which leads to the formulation of a thin, regular, well-defined and well-adhered intima on the inner surface of the prosthesis.

Although particular embodiments of the present invention have been described and illustrated herein, it is recognized that modifications and variations may readily occur to those skilled in the art and consequently, it is intended that the claims be intended to cover such modifications and equivalents.

What is claimed is:

1. A vascular prosthesis, comprising
   a base material having inner and outer surfaces and a degree of porosity,
   an outer coating of compounded heparin bound to said outer surface of said base material and an inner coating of compounded heparin bound to said inner surface of said base material, said compounded heparin including heparin and a cationic surfactant, and
   a layer of a material capable of reducing said degree of porosity of said base material formed on said outer coating of compounded heparin, said layer of material being free of any substance that counteracts an anti-coagulant.

2. The vascular prosthesis as claimed in claim 1, wherein said material capable of reducing said degree of porosity of said base material is a biodegradable material.

3. The vascular prosthesis as claimed in claim 2, wherein said biodegradable material is collagen.

4. The vascular prosthesis as claimed in claim 1, wherein said material capable of reducing said degree of porosity of said base material is a non-biodegradable material.

5. The vascular prosthesis as claimed in claim 4, wherein said non-biodegradable material is a silicon-based polymer.

6. The vascular prosthesis as claimed in claim 1, wherein said base material is a bio-compatible polymeric material.

7. The vascular prosthesis as claimed in claim 6, wherein said bio-compatible polymeric material is polyethylene terephthalate.

8. The vascular prosthesis as claimed in claim 7, wherein said polyethylene terephthalate is woven.

9. The vascular prosthesis as claimed in claim 7, wherein said polyethylene terephthalate is knitted.

10. The vascular prosthesis as claimed in claim 1, wherein said base material has a tubular shape.

11. The vascular prosthesis as claimed in claim 10, wherein said tubular shape is radially supported by a synthetic polymer.

12. The vascular prosthesis as claimed in claim 11, wherein said synthetic polymer includes a polypropylene monofilament spirally wound along a length of said tubular shape.

13. The vascular prosthesis as claimed in claim 1, wherein said base material has a bifurcated tubular shape.

14. The vascular prosthesis as claimed in claim 13, wherein said bifurcated tubular shape is radially supported by a synthetic polymer.

15. The vascular prosthesis as claimed in claim 14, wherein said synthetic polymer includes a polypropylene monofilament spirally wound along a length of said tubular shape.

16. The vascular prosthesis as claimed in claim 1, wherein said base material has a planar shape.

17. The vascular prosthesis as claimed in claim 16, wherein said base material comprises a narrow strip having selvedged edges.

18. The vascular prosthesis as claimed in claim 1, wherein said compounded heparin includes heparin ionically bonded with tridodecylmethylammonium chloride.

19. The vascular prosthesis as claimed in claim 1, wherein said compounded heparin includes heparin ionically bonded with benzalkonium chloride.

20. A method of forming a vascular prosthesis, comprising the steps of:

providing a base material having inner and outer surfaces and a degree of porosity;

applying a compounded heparin coating to said inner surface of said base material, applying a compounded heparin coating to said outer surface of said base material, and applying to said outer surface of said base material overlying said compounded heparin coating a layer of a material capable of reducing said degree of porosity of said base material, said layer of material being free of any substance that counteracts an anti-coagulant, wherein said compounded heparin includes heparin and a cationic surfactant.

* * * * *